United States Patent [19]
Elff et al.

[11] Patent Number: 5,263,076
[45] Date of Patent: Nov. 16, 1993

[54] LITHOTRIPSY WORKSTATION

[75] Inventors: Manfred Elff, Manburg; Dietrich Dirks, Norderstedt; Wilfried Pfeiffer, Quickborn; Siegfried Schmidt, Hamburg, all of Fed. Rep. of Germany

[73] Assignee: U.S. Philips Corp., New York, N.Y.

[21] Appl. No.: 853,367

[22] Filed: Mar. 18, 1992

[30] Foreign Application Priority Data

Apr. 13, 1991 [DE] Fed. Rep. of Germany ....... 4112148

[51] Int. Cl.$^5$ .............................................. A61B 17/00
[52] U.S. Cl. .................... 378/162; 378/163; 378/205
[58] Field of Search ............... 378/162, 163, 164, 204, 378/205; 128/328

[56] References Cited
U.S. PATENT DOCUMENTS 4,722,336 2/1988 Kim et al. ............................ 378/162
4,819,257 4/1989 Grasser et al. ...................... 378/205
4,930,509 6/1990 Brisson ................................ 128/653

FOREIGN PATENT DOCUMENTS 0286170 10/1988 European Pat. Off. .
3919083 6/1990 Fed. Rep. of Germany .

Primary Examiner—David P. Porta
Attorney, Agent, or Firm—Jack D. Slobod

[57] ABSTRACT

A lithotripsy workstation, comprises a patient supporting device (1), a shockwave source (4) for generating shockwaves which are focused onto a point (focus) (6) fixed in space, an X-ray source (10) which irradiates the focus (6) from at least two defined positions, and an image detector (12) which detects the X-ray image produced by the X-ray source (10). The cost and the weight of the workstation can be reduced in that a marker (16) which can be displayed in the X-ray image is secured to the X-ray source (10), which marker is situated, at least in the two positions, on the connecting line between the focal spot (11) of the X-ray source (10) and the focus (6).

18 Claims, 2 Drawing Sheets

LITHOTRIPSY WORKSTATION

FIELD OF THE INVENTION

The invention relates to a lithotripsy workstation, comprising a patient supporting device, a shockwave source for generating shockwaves focused onto a fixed point in space (focus), an X-ray source which irradiates the focus from at least two positions defined relative to the focus, and an image detector which detects the X-ray image produced by the X-ray source.

BACKGROUND OF THE INVENTION

A lithotripsy workstation of this kind is known from EP-A-286 170. Therein, the X-ray source and the image pick-up device are mounted on a U-arm which encompasses the table top of the patient supporting device and which is pivotable about a horizontal axis extending perpendicularly to the longitudinal direction of the table top. The U-arm is journalled in a stand. The shockwave generator is arranged so that its focus is situated at the point of intersection between the axis and the central ray.

In the known device it is comparatively easy to position a patient so that the (renal) calculus to be crushed is situated in the focus of the shockwave generator. In a first position in which the central ray extends perpendicular the patient is positioned so that the calculus is projected exactly onto the marked center of the image pick-up device, e.g. an X-ray image intensifier. The calculus is then situated in the central ray, but may still be situated above or underneath the focus. Therefore, in a second position of the U-arm, in which the central ray extends obliquely, the table top is lifted or lowered until the calculus is again situated in the center of the image intensifier which can be made visible in the X-ray image by way of cross-hairs or the like. The calculus is then situated in the focus of the shockwave generator.

In order to achieve the necessary positioning accuracy, the mechanical stability of the U-arm and the stand supporting this arm must be high. Therefore, the U-arm and the stand have an expensive and heavy construction. Moreover, the U-arm impedes access to the patient at the side of the patient table device where the stand is situated.

SUMMARY OF THE INVENTION

It is an object of the present invention to construct a workstation of the kind set forth so that positioning can be performed as easily and accurately as in the known device, be it with less severe requirements imposed as regards mechanical precision.

This object is achieved in accordance with the invention in that a marker which can be displayed in the X-ray image is connected to the X-ray source or to a member rigidly connected thereto, which marker is situated, at least in the two (localization) positions, on the connecting line between the focal spot of the X-ray source and the focus.

In accordance with the invention, the positioning accuracy that can be achieved is dependent only on the fact that the marker, at least in the two positions wherefrom the focus is irradiated, is situated on the connecting line between the focal spot of the X-ray source and the focus of the shockwave source. Accurate alignment of the X-ray source and the image detector, however, is not important for the positioning accuracy. The supports for these components, therefore, may be less stable and hence less heavy and less expensive than in the known device.

It is to be noted that the use of markers that can be displayed in the X-ray image in a lithotripter is already known from DE-PS-39 19 083. In the known apparatus the X-ray source and the image detector are aligned relative to one another by mounting on a C-arm. The C-arm is movable independently of the shockwave source, so that the X-ray source does not occupy a defined position relative to the focus.

In order to achieve accurate positioning nevertheless, on the shockwave source there is mounted a sight which comprises (at least) four markers, each two of which are arranged on straight lines which intersect in the focus. For the positioning of the patient the C-arm is moved to such a position that its central ray coincides with one of the two straight lines. Because this cannot be accurately achieved in practice, the two markers are imaged in different positions on the image detector or a monitor coupled thereto. From the position of the markers, to be input by the operator by means of a light pen, a computer can calculate the position of the focus on the display screen so as to map a suitable electronic mark at the position calculated. The operator must subsequently displace the patient on the patient supporting device until the calculus is displayed in the same position as the electronic mark of the focus. The same procedure must subsequently be repeated for the other direction.

This positioning operation, where two markers and the electronically marked focus appear in the monitor image, is very intricate for the user. The displaceable C-arm impedes access to the patient even more than in the described known apparatus comprising a U-arm which is pivotable about an axis fixed in space.

In a further embodiment of the invention, the X-ray source is movable along a path in the form of a circular arc whose center of curvature is situated in the focus. The X-ray source could in principle also be displaced from one position to the other position along a rectilinear path; in that case it would be necessary to pivot the X-ray source and/or the marker so that the marker is situated on the connecting line also in the other position. However, in the further embodiment the marker is situated on the connecting line in any position, so that it is not necessary to move the X-ray source exactly to the two positions for accurate positioning.

A path in the form of a circular arc about the focus could be realized, for example, by connecting the X-ray source to an arm which is pivotable about a horizontal axis extending through the focus. In a further embodiment, however, the X-ray source can be moved along a path in the form of a circular arc in a substantially simpler manner by utilizing a guide rail on which the source is displaceable and which describes a circular arc about the focus. Such a guide rail could be arranged, for example underneath the patient supporting device where it does not impede the access to the patient.

In another embodiment of the invention, the image detector is connected to a ceiling stand. It is thus ensured that the supporting means for the image detector do not impede the access to the patient either.

Because it is not important for accurate positioning that the X-ray source and the image detector are exactly aligned relative to one another, the image detector may remain stationary during displacement of the X-ray source, provided that its entrance face is large enough to collect the X-ray image in any position of the X-ray source. In a further embodiment, however, a smaller image detector suffices by using a control device which matches the movements of the image detector and the X-ray source in such a manner that the marker is projected, at least in the two positions of the X-ray source, onto a small area around the center of the entrance face of the image detector. The image detector can be tilted so that the X-rays are incident thereon at right angles. However, it is alternatively possible to abstain from tilting the image detector during its movement, so that the direction of its optical axis is not changed.

BRIEF DESCRIPTION OF THE DRAWING

The invention will be described in detail hereinafter with reference to the drawings. Therein.

BRIEF DESCRIPTION OF THE PREFERRED EMBODIMENT

Figure 1:
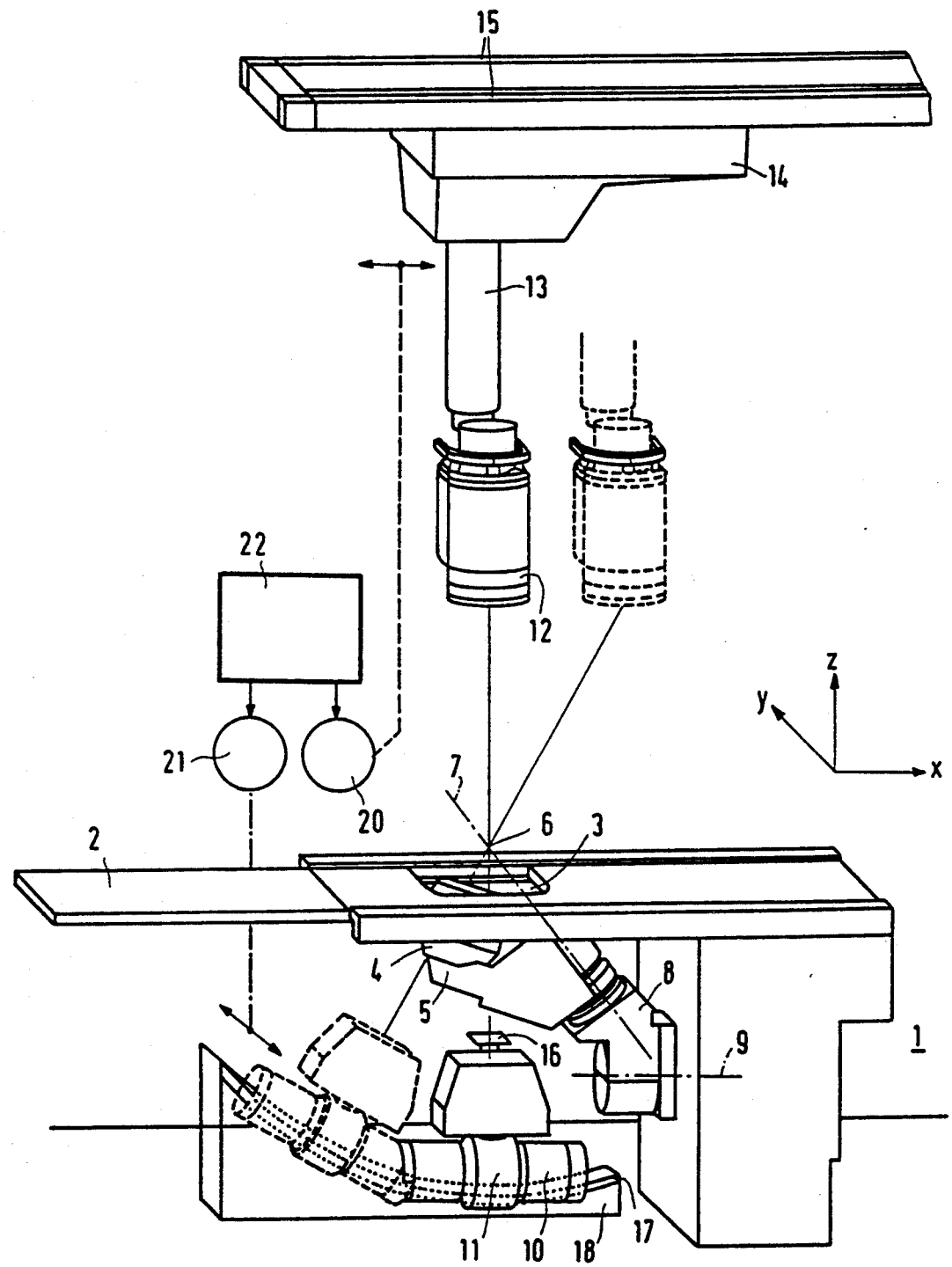
FIG. 1 shows a preferred embodiment of the invention.

The lithotripsy workstation shown in FIG. 1 comprises a patient supporting device which includes a table top 2 in which there is provided an opening 3 wherethrough shockwaves can be directed onto a patient 24 (FIG. 2) from a shockwave generator 4 arranged underneath the table top 2. The table top 2 is displaceable, in a manner not shown, in the x, y and z-directions, the x-direction corresponding to the longitudinal direction of the table, while the y-direction corresponds to the horizontal direction perpendicular thereto and the z-direction corresponds to the vertical direction.

The shockwave generator 4 delivers shockwaves which are focused onto a point 6, being the so-called focus. It is secured to a pivot arm 5 which is pivotable about an axis 7 extending through the focus 6 at an angle to the horizontal plane. The shockwave generator 4 can thus be pivoted about the axis 7 without the position in space of its focus 6 being changed. The pivot arm 5 is connected to a bearing support 8 which is pivotable about an axis 9 which extends in the x-direction underneath the pivot arm 5. The shockwave source can thus be completely pivoted to the side.

The lithotripsy workstation described thus far is known from EP-OS-286 170. For the advantages obtained by the fact that the shockwave source is pivotable about the axes 7 and 9, reference is made to the cited publication.

Underneath the table top there is arranged an X-ray source 10 whose focal spot 11 emits a radiation beam in the operating condition, which beam images the area around the focus 6 on the entrance screen of an X-ray image intensifier 12. The X-ray image intensifier 12 is connected to a ceiling stand 13 so as to be displaceable in the z-direction, which stand is displaceable on a carriage 14 on rails 15 extending in the x-direction.

On the X-ray source 10 or on its support there is mounted a marker 16 which is situated at a distance from the focal spot 11 (for example, 300 mm). The marker 16 may be a system of cross-hairs which is formed by (heavy) metal strips on a plate which is transparent to X-rays and which extends perpendicular to the central ray. The marker, or the cross-hairs, is arranged on the connecting line between the focal spot 11 and the focus 6, so that the projection of the cross-hairs on the entrance screen of the X-ray image intensifier 12 characterizes the position of the focus 6.

The X-ray source 10 is displaceable on a guide rail 17 of a guide system 18 which is arranged on the floor underneath the table top 2. The guide rail 17 is curved about an axis extending in the y-direction through about the focus 6, so that during displacement the focal spot 11 of the X-ray beam 10 follows a circular path about the focus 6 and the marker 16 which is rigidly connected to the source 10 always remains on the connecting line between the focus 6 and the focal spot 11.

The dashed lines show the source 10 in a position which is reached after the displacement of the source from the position denoted by solid lines (in which the connecting line between focus 6 and spot 11 extends perpendicular) to a position in which the connecting line extends at an angle of 30° relative to the vertical. The image intensifier 12 must then be moved so that the X-ray image produced by the X-ray source remains positioned on the entrance face of the image intensifier; however, it is not necessary for the cross-hairs to be projected onto the same location of the image intensifier entrance screen. As opposed to the known devices pivoting of the image intensifier so that its entrance face extends perpendicular to the central ray is not necessary either.

As is indicated by dash-dot lines, the carriage 14 and the X-ray source 10 are displaced by means of a respective motor 20, 21. A control device 22 ensures that the image intensifier 12 and the X-ray source 10 are always displaced so that X-ray beam is incident on the entrance face of the image intensifier 12.

The positioning will be described hereinafter with reference to the FIGS. 2 and 3 in which the shockwave source has been omitted for the sake of simplicity.

Figure 2:
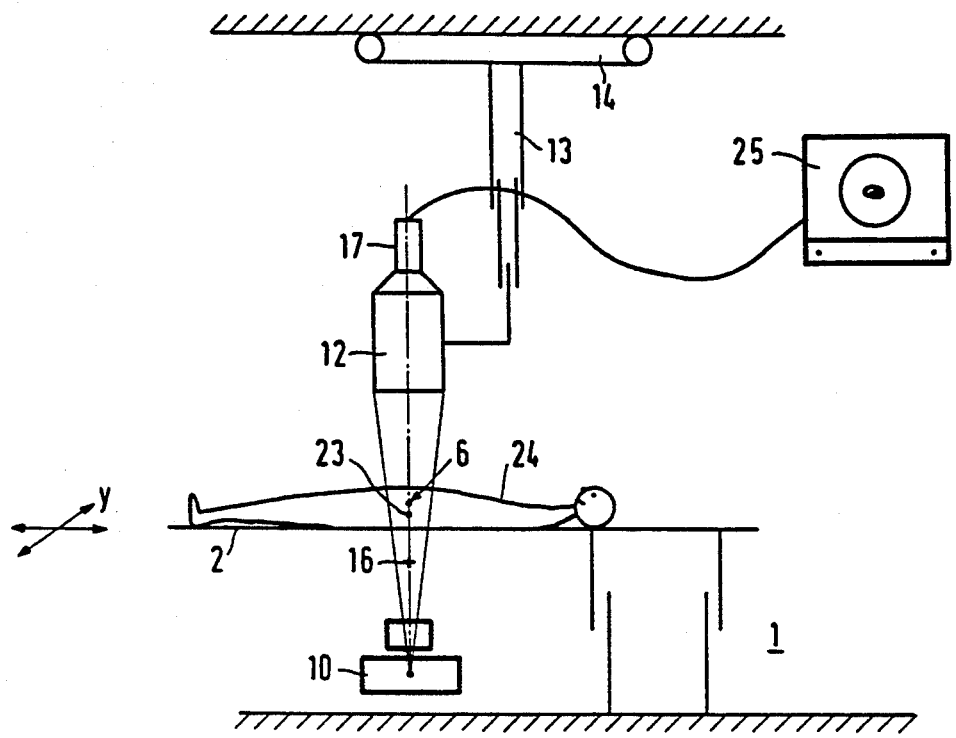
FIGS. 2 and 3 diagrammatically show the apparatus in accordance with the invention with different positions of the X-ray source and the image detector.

FIG. 2 diagrammatically shows the device of FIG. 1 in the case of a beam path perpendicular to the intensifier 12 entrance screen and to the horizontal plane. The X-ray beam emitted by the X-ray source 10 produces an X-ray image on the entrance face of the image intensifier 12, which image contains the cross-hairs 16 as well as a (renal) calculus 23 which is present in the patient 24 to be treated and which is to be crushed by the shockwave generator after the positioning opertion. The visible image produced at the image intensifier exit is picked up by a television camera 17 for display on a monitor 25. The user displaces the table top in the x-direction and the y-direction until the images of the marker 16 and the calculus 23 register on the monitor 25. The calculus is then situated on the vertical connecting line between the focal spot of the X-ray source 10 and the focus 6.

Figure 3:
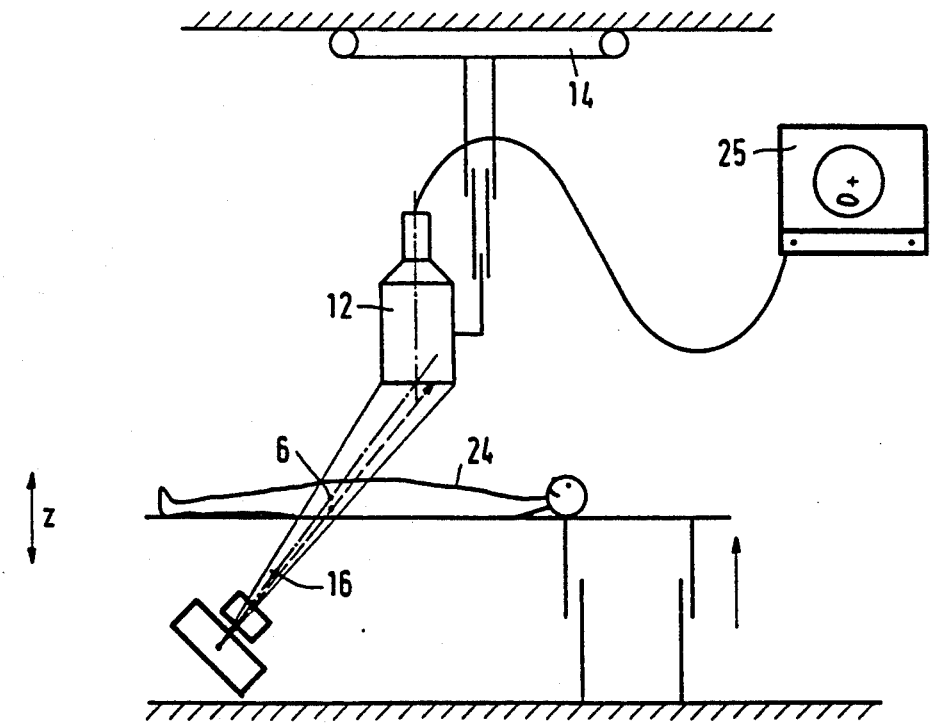

FIG. 3 shows the device after the pivoting of the X-ray source through approximately 30°. Because the calculus 23 is situated underneath the focus 6, the calculus and the cross-hairs do not register in the monitor image. The operator should then displace the table top only in the vertical direction (raising or lowering) until the images of the cross-hairs and the calculus on the monitor register. The calculus is then situated in the focus and the treatment may commence.

The invention has been described with reference to a device in which the X-ray source is situated underneath the table top 2 and the image intensifier is situated above the table top 2. However, the invention can also be used for lithotripsy workstations in which the X-ray source is situated above and the image intensifier is situated underneath the table top. Instead of being connected to the X-ray source itself, the marker 16 may also be connected to a member rigidly connected to the X-ray source, for example, to its support (not shown).

We claim:

1. A lithotripsy workstation comprising a patient supporting device, a shockwave source for generating shockwaves focused onto a focus fixed in space which focus is to be positioned within a patient supported by said patient supporting device, an X-ray source having a focal spot and which is moveable for successively irradiating the focus from two different positions defined relative to the focus, an image detector for detecting X-ray images produced by the successive irradiating of the focus by the X-ray source, said image detector not being rigidly coupled to said X-ray source, and a marker rigidly coupled to the X-ray source, which marker is situated, at least in the two positions, on a connecting line between the focal spot of the X-ray source and the focus.

2. A lithotripsy workstation as claimed in claim 1, further comprising including means for moving the X-ray source between said two positions along a circular arc path, the focus being situated at a center of curvature of the circular arc path.

3. A lithotripsy workstation as claimed in claim 2, wherein said moving means comprises a guide rail on which the X-ray source is displaceable and which describes a circular arc about the focus.

4. A lithotripsy workstation as claimed in claim 1 including a ceiling stand, said image detector being connected to the ceiling stand.

5. A lithotripsy workstation as claimed in claim 4 including means for moveably mounting the image detector and a control means which matches the movements of the image detector having an entrance face and the X-ray source so that the marker is projected, at least in the two positions of the X-ray source, onto an area around the center of the entrance face of the image detector.

6. A lithotripsy workstation as claimed in claim 1 wherein the shockwave generator is arranged underneath the patient supporting device and is pivotable about a first inclined axis which extends through the focus and which forms a vertical plane in conjunction with a longitudinal direction of the patient supporting device.

7. A lithotripsy workstation as claimed in claim 6, wherein the shockwave generator is supported by a pivot arm whose support is pivotable about a second axis which extends in the vertical plane underneath the support.

8. A lithotripsy workstation as claimed in claim 5, wherein the direction of the optical axis of the image detector is not changed during movement of the image detector.

9. A lithotripsy workstation as claimed in claim 3 including a ceiling stand, said image detector being connected to the ceiling stand.

10. A lithotripsy workstation as claimed in claim 1 including means for moveably mounting the image detector and a control means which matches the movements of the image detector having an entrance face and the X-ray source so that the marker is projected, at least in the two positions of the X-ray source, onto an area around the center of the entrance face of the image detector.

11. A lithotripsy workstation as claimed in claim 2 including means for moveably mounting the image detector and a control means which matches the movements of the image detector having an entrance face and the X-ray source so that the marker is projected, at least in the two positions of the X-ray source, onto an area around the center of the entrance face of the image detector.

12. A lithotripsy workstation as claimed in claim 3 including means for moveably mounting the image detector and a control means which matches the movements of the image detector having an entrance face and the X-ray source so that the marker is projected, at least in the two positions of the X-ray source, onto an area around the center of the entrance face of the image detector.

13. A lithotripsy workstation as claimed in claim 2 wherein the shockwave generator is arranged underneath the patient supporting device and is pivotable about a first inclined axis which extends through the focus and which forms a vertical plane in conjunction with a longitudinal direction of the patient supporting device.

14. A lithotripsy workstation as claimed in claim 4 wherein the shockwave generator is arranged underneath the patient supporting device and is pivotable about a first inclined axis which extends through the focus and which forms a vertical plane in conjunction with a longitudinal direction of the patient supporting device.

15. A lithotripsy workstation as claimed in claim 5 wherein the shockwave generator is arranged underneath the patient supporting device and is pivotable about a first inclined axis which extends through the focus and which forms a vertical plane in conjunction with a longitudinal direction of the patient supporting device.

16. A lithotripsy workstation as claimed in claim 12 wherein the shockwave generator is arranged underneath the patient supporting device and is pivotable about a first inclined axis which extends through the focus and which forms a vertical plane in conjunction with a longitudinal direction of the patient supporting device.

17. A lithotripsy workstation as claimed in claim 16 wherein the shockwave generator is supported by a pivot arm whose support is pivotable about a second axis which extends in the vertical plane underneath the support.

18. A lithotripsy workstation as claimed in claim 12 wherein the direction of the optical axis of the image detector is not changed during movement of the image detector.

* * * * *